(12) United States Patent
Cheng et al.

(10) Patent No.: US 12,138,127 B2
(45) Date of Patent: Nov. 12, 2024

(54) PORTABLE REMOTE ULTRASOUND SCANNING SYSTEMS AND COMPLIANCE CONTROL METHODS FOR SAFE ULTRASOUND SCANNING

(71) Applicant: HEFEI HEBIN INTELLIGENT ROBOTS CO., LTD., Anhui (CN)

(72) Inventors: Dongliang Cheng, Hefei (CN); Zhen Liu, Hefei (CN)

(73) Assignee: HEFEI HEBIN INTELLIGENT ROBOTS CO., LTD., Hefei (CN)

( * ) Notice: Subject to any disclaimer, the term of this patent is extended or adjusted under 35 U.S.C. 154(b) by 0 days.

(21) Appl. No.: 18/425,261

(22) Filed: Jan. 29, 2024

(65) Prior Publication Data

US 2024/0164759 A1 May 23, 2024

Related U.S. Application Data

(63) Continuation-in-part of application No. PCT/CN2022/117694, filed on Sep. 8, 2022.

(30) Foreign Application Priority Data

Oct. 14, 2021 (CN) .......................... 202111199054.1

(51) Int. Cl.
*A61B 8/00* (2006.01)
*A61B 90/00* (2016.01)
(Continued)

(52) U.S. Cl.
CPC .............. *A61B 8/54* (2013.01); *A61B 8/4218* (2013.01); *A61B 8/4254* (2013.01); *A61B 8/429* (2013.01);
(Continued)

(58) Field of Classification Search
CPC ......... A61B 34/32; A61B 34/37; A61B 34/30; A61B 2090/065; A61B 8/429; B25J 9/1666
See application file for complete search history.

(56) References Cited

U.S. PATENT DOCUMENTS

| 6,425,865 B1 | 7/2002 | Salcudean et al. |
| 2010/0041991 A1* | 2/2010 | Roundhill ............. A61B 8/467 600/443 |

(Continued)

FOREIGN PATENT DOCUMENTS

| CN | 101610721 A | 12/2009 |
| CN | 103829973 A | 6/2014 |

(Continued)

OTHER PUBLICATIONS

First Office Action in Chinese Application No. 202111199054.1 mailed on Sep. 27, 2022, 20 pages.
(Continued)

*Primary Examiner* — Jeffrey G Hoekstra
*Assistant Examiner* — Nyrobi Celestine
(74) *Attorney, Agent, or Firm* — Porus IP LLC (57) ABSTRACT

A portable remote ultrasound scanning system is disclosed. A master device includes a handheld device and a master computer. A slave device includes a slave scanning robot, a slave ultrasound device, a slave environment sensing unit, and a data transceiver unit. The handheld device is configured to send velocity information of a movement of the handheld device, angular velocity information of a rotation of the handheld device, and a pressing force to a controller of the slave scanning robot through the master computer and the data transceiver unit. The controller is configured to control a movement of the robotic arm in a horizontal plane, an orientation movement of the robotic arm in space, and a movement of the robotic arm along a normal direction of a (Continued)

scanning surface. The master computer displays an ultrasound scanning image. An entire movement process of the robotic arm is performed through a compliance control.

8 Claims, 2 Drawing Sheets

(51) Int. Cl.
  *B25J 3/04* (2006.01)
  *B25J 9/16* (2006.01)
  *B25J 13/02* (2006.01)
  *B25J 13/08* (2006.01)
  *G16H 40/67* (2018.01)

(52) U.S. Cl.
  CPC .......... *A61B 8/4416* (2013.01); *A61B 8/4427* (2013.01); *A61B 8/461* (2013.01); *A61B 8/56* (2013.01); *B25J 3/04* (2013.01); *B25J 9/1666* (2013.01); *B25J 13/025* (2013.01); *B25J 13/085* (2013.01); *G16H 40/67* (2018.01); *A61B 2090/065* (2016.02); *A61B 2090/066* (2016.02)

(56) References Cited

U.S. PATENT DOCUMENTS

| | | |
|---|---|---|
| 2015/0366546 A1 | 12/2015 | Kamen et al. |
| 2017/0143303 A1 | 5/2017 | Chen et al. |
| 2017/0202537 A1* | 7/2017 | Ippolito ................. A61B 34/76 |
| 2017/0304007 A1* | 10/2017 | Piron ..................... A61B 1/045 |
| 2019/0090967 A1* | 3/2019 | Guthart ................... A61B 1/04 |
| 2020/0008880 A1* | 1/2020 | Jang ........................ A61B 34/37 |
| 2020/0179069 A1* | 6/2020 | Keller .................... B25J 9/1633 |
| 2020/0194117 A1* | 6/2020 | Krieger .................. A61B 8/429 |
| 2021/0093407 A1 | 4/2021 | Fredrickson et al. |

FOREIGN PATENT DOCUMENTS

| | | |
|---|---|---|
| CN | 107157512 A | 9/2017 |
| CN | 209004045 U | 6/2019 |
| CN | 109998590 A | 7/2019 |
| CN | 110755110 A | 2/2020 |
| CN | 110993087 A | 4/2020 |
| CN | 108994861 B | 1/2021 |
| CN | 112206006 A | 1/2021 |
| CN | 112215843 A | 1/2021 |
| CN | 112274178 A | 1/2021 |
| CN | 112754517 A | 5/2021 |
| CN | 112998749 A | 6/2021 |
| CN | 113842165 A | 12/2021 |
| WO | 2011115287 A1 | 9/2011 |

OTHER PUBLICATIONS

Notification to Grant Patent Right for Invention in Chinese Application No. 202111199054.1 mailed on Nov. 29, 2022, 5 pages.
International Search Report in PCT/CN2022/117694 mailed on Nov. 22, 2022, 7 pages.
Written Opinion in PCT/CN2022/117694 mailed on Nov. 22, 2022, 8 pages.

* cited by examiner

PORTABLE REMOTE ULTRASOUND SCANNING SYSTEMS AND COMPLIANCE CONTROL METHODS FOR SAFE ULTRASOUND SCANNING

CROSS-REFERENCE TO RELATED APPLICATIONS

This application is a continuation-in-part of International Application No. PCT/CN2022/117694, filed on Sep. 8, 2022, which claims the priority of Chinese patent application No. 202111199054.1, filed on Oct. 14, 2021, entitled "PORTABLE REMOTE ULTRASOUND SCANNING SYSTEMS AND COMPLIANCE CONTROL METHODS FOR SAFE ULTRASOUND SCANNING", the entire contents of each of which are hereby incorporated by reference.

TECHNICAL FIELD

The present disclosure relates to the technical field of remote ultrasound scanning, and in particular, to a portable remote ultrasound scanning system and a compliance control method for safe ultrasound scanning.

BACKGROUND

The remote ultrasound scanning systems available now include a master device and a slave scanning robot. A physician remotely controls the slave scanning robot to perform an ultrasound examination through the master device.

Retrieved Chinese Patent with publication No. CN109998590A discloses a remote ultrasound operation system and a method for controlling the remote ultrasound operation system, in which a remote operation device, i.e., the master device, includes a human body forming device and an operating hand. The human body forming device is configured to receive a 3D data signal collected by a 3D scanner and generate a similar-shaped body to a region to be examined of a patient based on the 3D data signal.

Retrieved Chinese Patent with issued No. CN108994861B discloses a remote ultrasound operating hand device and a remote ultrasound detection system, in which an operating hand obtains spatial location information of the operating hand by touching a location sensor through a bottom of the operating hand, i.e., the operating hand must move on a touch screen provided with the location sensor to obtain the spatial location information.

Retrieved Chinese Patent with publication No. CN110993087A discloses a device and a method for manipulating remote ultrasound scanning, in which a master device includes a simulated skin platform that simulates movement of an actual ultrasound probe on the skin. The master device obtains 2D coordinates of a simulated ultrasound probe on a surface of the simulated skin platform and remotely controls a movement of the ultrasound probe on the skin based on the 2D coordinates.

In summary, the remote ultrasound scanning systems available now have the following problems: the operation device on the physician's end (i.e., the master device) is complex and immovable once installed, and requires a specific working plane to simulate the movement of the ultrasound probe on the skin, which makes operation device inconvenient to be carried around.

Additionally, the remote ultrasound scanning systems available now also have the following problems:

The technical methods adopted for the master device and the slave scanning robot often involve a position mapping and a segmental force control mapping. The position mapping cannot ensure continuity of a movement of the slave scanning robot and segmental force control mapping cannot ensure continuity of an end force.

The slave scanning robot cannot achieve joint force control and full-process compliance control.

The physician cannot obtain contact force information between the ultrasound probe and a scanned region of a human body from the master device.

SUMMARY

In order to overcome the above mentioned defects in the prior art, the present disclosure provides a portable remote ultrasound scanning system, which utilizes a master device to remotely control a slave scanning robot to perform an ultrasound examination.

For the above purposes, the present disclosure adopts the following technical solution, including:

A portable remote ultrasound scanning system, including a master device and a slave device.

The master device includes a handheld device and a master computer connected to the handheld device.

The slave device includes a slave scanning robot, a slave ultrasound device, and a data transceiver unit connected to the slave scanning robot and the slave ultrasound device respectively.

The handheld device is configured to send trajectory information of the handheld device to the master computer, the handheld device is configured further to send a pressing force exerted on the handheld device to the master computer, the trajectory information of the handheld device including velocity information of the handheld device moving on a working plane and angular velocity information of a rotation of the handheld device in space.

The master computer communicates with the data transceiver unit, and the master computer is configured to send the trajectory information of the handheld device and the pressing force exerted on the handheld device to the data transceiver unit.

The slave ultrasound device is configured to perform an ultrasound scanning, collect an ultrasound image, and send the ultrasound image to the data transceiver unit, and the data transceiver unit is configured to send the ultrasound image to the master computer.

The slave ultrasound device includes an ultrasound probe.

The slave scanning robot includes a robotic arm and a controller configured to control a movement of the robotic arm.

The ultrasound probe is provided at an end of the robotic arm.

The data transceiver unit is configured to send the trajectory information of the handheld device and the pressing force exerted on the handheld device to the controller.

The controller is configured to control a movement of an end effector of the robotic arm in a horizontal plane based on the velocity information of the handheld device moving on the working plane such that a movement velocity of the ultrasound probe at the end of the robotic arm in the horizontal plane is the same as a movement velocity of the handheld device on the working plane.

The controller is configured to control an orientation movement of the end effector of the robotic arm in space based on the angular velocity information of the rotation of the handheld device in space such that a rotational angular velocity of the ultrasound probe at the end of the robotic arm in space is the same as a rotational angular velocity of the handheld device in space.

The controller is configured to control, based on the pressing force exerted on the handheld device, the end effector of the robotic arm to move along a normal direction of a scanning surface such that a contact force between the ultrasound probe at the end of the robotic arm and a scanned region of a human body (i.e., an actual contact force of the ultrasound probe) is the same as the pressing force exerted on the handheld device.

An entire movement process of the robotic arm is performed through a compliance control.

The end of the robotic arm is provided with a depth camera configured to capture a depth image; and the depth camera is connected to the controller and configured to send the depth image to the controller, and the controller is configured to send the depth image to the master computer through the data transceiver unit.

The depth camera is configured to capture the depth image of a surface of the human body; the master computer is configured to perform a three-dimensional modeling of the human body based on the depth image of the surface of the human body to obtain a three-dimensional model of the human body; the master computer is configured to identify the scanned region of the human body based on the three-dimensional model of the human body, set an initial position for ultrasound scanning of the scanned region of the human body, generate a collision-free path for the robotic arm from a current position to the initial scanning position based on the three-dimensional model and a path planning algorithm, and send the collision-free path to the controller through the data transceiver unit; and the controller is configured to control the end effector of the robotic arm to move along the collision-free path such that the ultrasound probe at the end of the robotic arm automatically reaches the initial position for ultrasound scanning.

The handheld device is configured to obtain the velocity information of the handheld device moving on the working plane through a photoelectric velocity sensor, and the movement of the end effector of the robotic arm in the horizontal plane is controlled through velocity mapping.

The data transceiver unit includes a robot data interface for data transmission with the slave scanning robot and an ultrasound data interface for data transmission with the slave ultrasound device.

The controller is configured to send the actual contact force of the ultrasound probe to the data transceiver unit, the data transceiver unit is configured to send the actual contact force of the ultrasound probe to the master computer, and the master computer is configured to send the actual contact force of the ultrasound probe to the handheld device.

The handheld device is provided with a display configured to display the actual contact force of the ultrasound probe, the pressing force exerted on the handheld device, and a difference between the actual contact force of the ultrasound probe and the pressing force exerted on the handheld device in real-time.

The handheld device is further provided with a vibration module, the vibration module being configured to generate vibrations according to the difference between the actual contact force of the ultrasound probe and the pressing force exerted on the handheld device, wherein the vibration module generates the vibrations when the difference is greater than a threshold, and the greater the difference, the greater the intensity of the vibrations.

The slave device further includes a slave environment sensing unit.

The slave environment sensing unit includes a global camera and a communication device.

The global camera is configured to obtain an overall video of the slave scanning robot and a position and orientation video of the robotic arm. The global camera is connected to the data transceiver unit and configured to send the overall video of the slave scanning robot and the position and orientation video of the robotic arm to the master computer through the data transceiver unit such that the overall video of the slave scanning robot and the position and orientation video of the robotic arm are displayed on the master computer in real-time.

The communication device is configured to realize real-time communication between a physician and a patient.

The robotic arm is provided with a torque sensor configured to obtain a joint torque of the robotic arm. The controller is connected to the torque sensor and configured to determine, based on the joint torque of the robotic arm obtained by the torque sensor, the contact force between the ultrasound probe at the end of the robotic arm and the scanned region of the human body (i.e., the actual contact force of the ultrasound probe).

The slave device has a coupling agent detection function. The coupling agent detection function may be used to detect whether a coupling agent is sufficient at at least one time point for each scanning position. The master computer is further configured to send an alert message to the physician based on a detection result of the coupling agent.

The present disclosure also provides a compliance control method for safe ultrasound scanning, wherein the entire movement process of the robotic arm is performed through the compliance control, specifically:

During a non-ultrasound scanning process, the movement of the robotic arm adopts an impedance control, i.e., the movement of the end effector of the robotic arm in the horizontal plane and a movement of the end effector of the robotic arm along the normal direction of the scanning surface are performed through the impedance control; and the non-ultrasound scanning process refers to a process where the controller controls the movement of the robotic arm such that the ultrasound probe reaches the scanned region of the human body, and during the non-ultrasound scanning process, the contact force between the ultrasound probe and the scanned region of the human body (i.e., the actual contact force of the ultrasound probe) is zero.

During an ultrasound scanning process, the movement of the robotic arm adopts a hybrid control of the impedance control and a constant force control, i.e., the movement of the end effector of the robotic arm in the horizontal plane is performed through the impedance control, and the movement of the end effector of the robotic arm along the normal direction of the scanning surface is performed through the constant force control; and the ultrasound scanning process refers to a process where the controller controls the movement of the robotic arm such that the ultrasound probe performs the ultrasound scanning on the scanned region of the human body, and during the ultrasound scanning process, the actual contact force between the ultrasound probe and the scanned region of the human body (i.e., the actual contact force of the ultrasound probe) is greater than zero.

During the ultrasound scanning process, the pressing force exerted on the handheld device is converted to a desired force value for the constant force control through a variable force segmental mapping or variable force continuous mapping, and the contact force between the ultrasound probe and the scanned region of the human body follows the desired force value.

The variable force segmental mapping refers to a process where the pressing force exerted on the handheld device is divided into different segments and each segment is mapped to the controller, and the controller controls the movement of the robotic arm to drive the ultrasound probe to perform the ultrasound scanning on the scanned region of the human body, wherein when the pressing force exerted on the handheld device falls within a certain segment, the desired force value for the constant force control remains unchanged and the desired force value is a certain value within the segment; and when the pressing force exerted on the handheld device switches to a different segment, the desired force value for the constant force control changes accordingly to a certain value within the different segment.

The variable force continuous mapping refers to a process where the pressing force exerted on the handheld device is continuously mapped to the controller in proportion, and the controller controls the movement of the robotic arm to drive the ultrasound probe to perform the ultrasound scanning on the scanned region of the human body, wherein the desired force value for the constant force control changes continuously following continuous changes of the pressing force exerted on the handheld device.

DETAILED DESCRIPTION

The technical solutions in the embodiments of the present disclosure will be clearly and completely described below in conjunction with the accompanying drawings in the embodiments of the present disclosure. Obviously, the described embodiments are only a part of the embodiments of the present disclosure and not all of the embodiments. Based on the embodiments of the present disclosure, all other embodiments obtained by those skilled in the art without creative effort fall within the scope of protection of the present disclosure.

Figure 1:
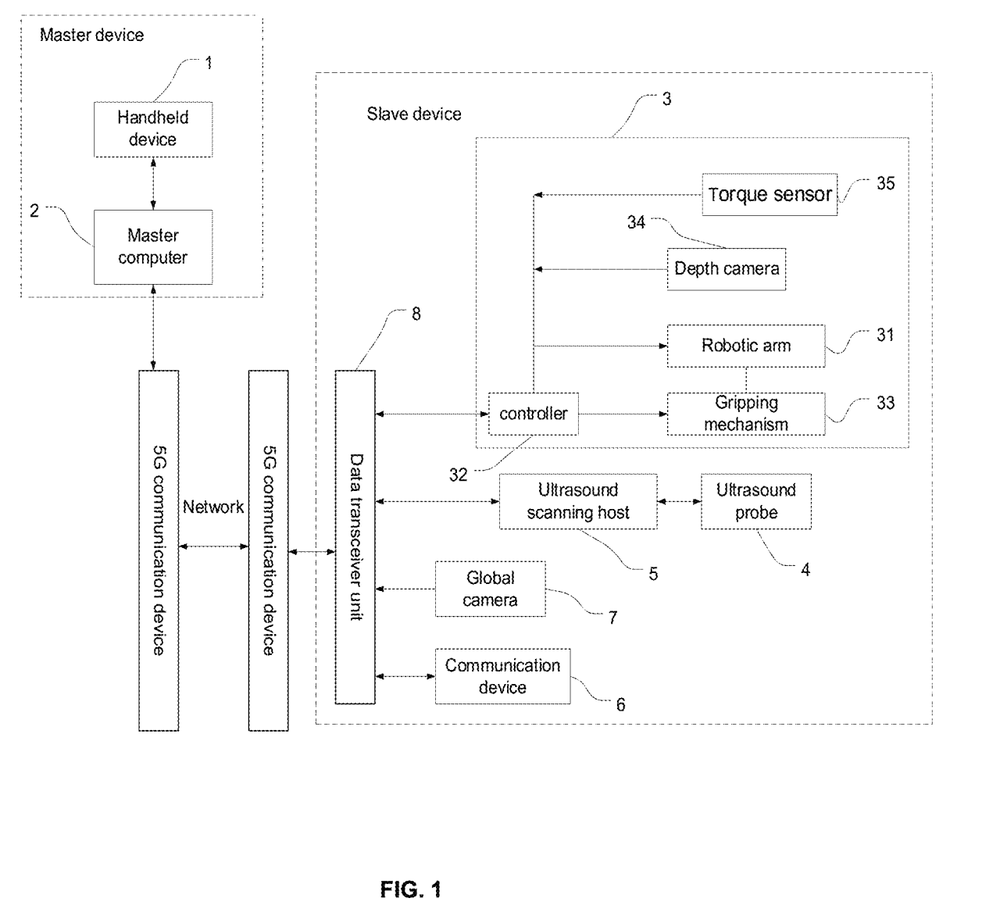
FIG. 1 is a structural diagram illustrating a portable remote ultrasound scanning system of the present disclosure.
Figure 2:
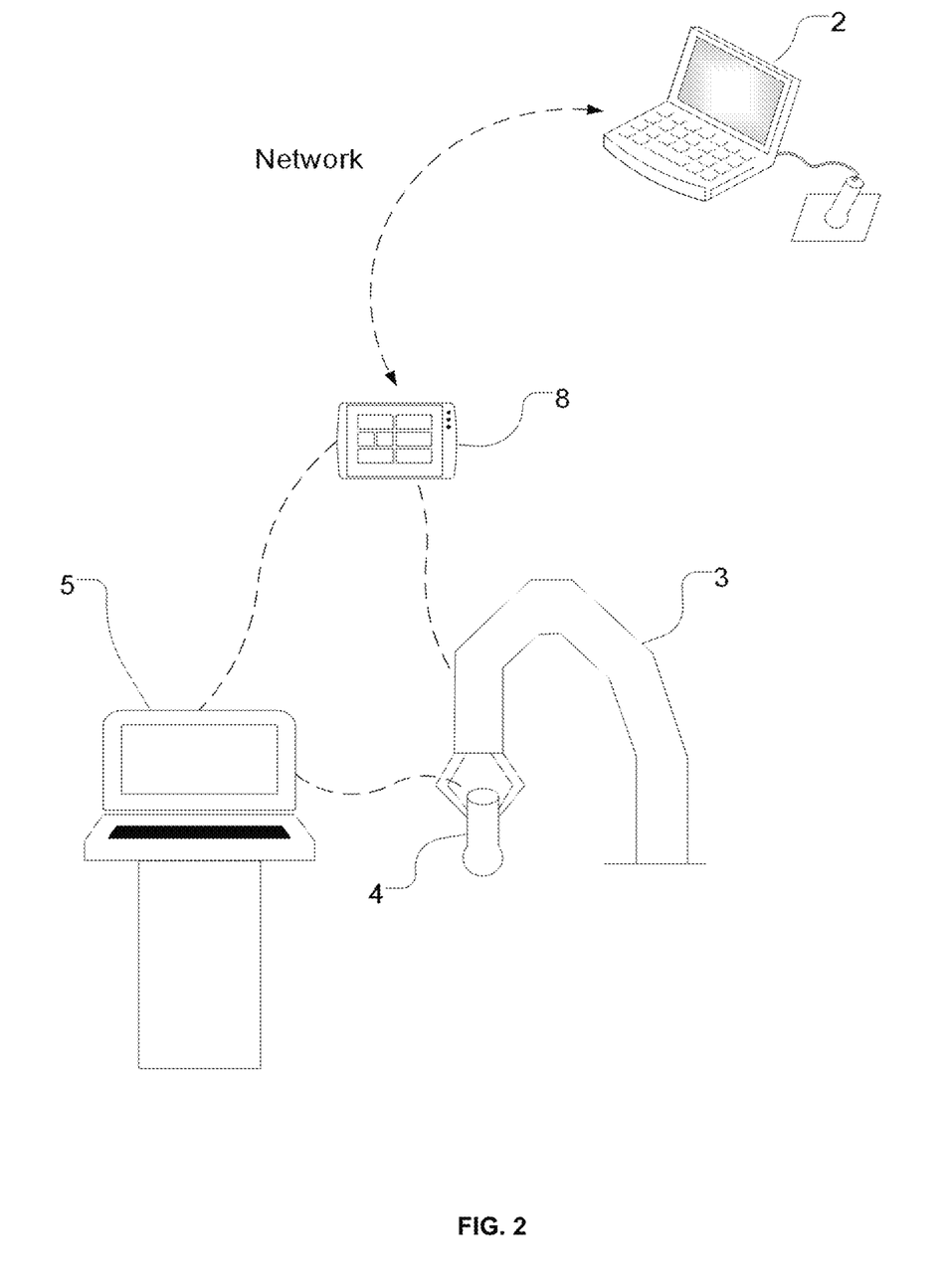
FIG. 2 is a schematic diagram illustrating an overall portable remote ultrasound scanning system of the present disclosure.

As shown in FIGS. 1 and 2, a portable remote ultrasound scanning system includes a master device and a slave device, wherein a master-end is a physician-end f remote control and a slave-end is a patient-end for ultrasound scanning.

The master device includes a handheld device 1 and a master computer 2 connected to the handheld device 1.

The slave device includes a slave scanning robot, a slave ultrasound device, a slave environment sensing unit, and a data transceiver unit 8 connected to the slave scanning robot, the slave ultrasound device, and the slave environment sensing unit respectively.

The handheld device 1 is configured to simulate an orientation movement of an ultrasound probe 4 in space. When a physician holds the handheld device 1 and moves the handheld device 1 on a working plane, for example, simulates the ultrasonic probe to perform a virtual ultrasonic scanning movement, the handheld device 1 obtains velocity information of the handheld device 1 moving on the working plane through a photoelectric velocity sensor; when the physician holds the handheld device 1 and rotates the handheld device 1 in space, the handheld device 1 obtains angular velocity information of a rotation of the handheld device in space through an orientation and angular velocity sensor.

The working plane refers to a surface of an object with which the handheld device may contact, such as a desktop, a surface of a human body skin model, a surface of a human body, etc.

In some embodiments, the handheld device 1 is a mimetic ultrasound probe, with a similar appearance to and a same operation manner as a real ultrasound probe (e.g., the ultrasound probe 4). When the physician remotely controls the slave ultrasound device (e.g., the ultrasound probe 4) using the handheld device 1, there are no constraints on an operating space and no change in the physician's operating habit(s), which allows the physician to simulate more realistic ultrasound scanning movement(s) without the need for additional learning and adaptation to the use of the handheld device, thereby reducing the cost of learning remote ultrasound scanning operations.

In some embodiments, the handheld device 1 has relatively small parameters such as weight and size, making it more portable and suitable for the physician's operations. For example, the handheld device 1 may have a weight of 0.18 kg, dimensions of 150 mm*65 mm*34 mm.

The handheld device 1 is configured to obtain trajectory information of the virtual ultrasound scanning movement and send the trajectory information to the master computer 2, wherein the trajectory information is the velocity information of the handheld device 1 moving on the working plane and the angular velocity information of the rotation of the handheld device in space.

The handheld device 1 is further configured to obtain a pressing force exerted on the handheld device 1 during the virtual ultrasound scanning movement through a pressure sensor and send the pressing force exerted on the handheld device 1 to the master computer 2.

The pressing force refers to a force between the handheld device and the work plane. For example, when the physician moves the handheld device 1 on the work plane, the force exerted on a contact surface between the handheld device 1 and the work plane is the pressing force. A reactive force of the pressing force may be directly fed back to the physician through the handheld device 1, similar to that the physician may directly perceive the pressing force exerted by an ultrasound probe on the surface of the human body when moving the ultrasound probe, i.e., a force feedback source for the handheld device 1 is the pressing force the handheld device 1 receives when the physician moves the handheld device 1 on the working plane. The force feedback does not require any mechanical or motorized structures.

In some embodiments of the present disclosure, the force feedback source and operation mode of the handheld device 1 is adjusted. The force feedback is achieved by utilizing the reactive force of the pressing force exerted on the handheld device 1 when the handheld device 1 moves on the working plane, which does not need to be based on an actual contact force of the ultrasound probe and does not require mechanical or motorized structures to convey the actual contact force of the ultrasound probe to the physician's hand, thereby reducing a structure of the handheld device, facilitating an integrated and portable design, and allowing operation on any working plane without restrictions. In addition, a need for an additional auxiliary device(s) such as a touch table can be eliminated, and when connected to a computer, the handheld device can forms the physician's end device or the master device. The structure is simple, easy to carry, and convenient for performing ultrasound scans on patients in a home environment. Furthermore, on the basis of portability, this design can ensure more timely and efficient force feedback, contributing to a more immediate haptic sensation for the physician during ultrasound scanning. In some embodiments, although the master computer 2 obtains the actual contact force of the ultrasound probe 4, the actual contact force is not used to generate the force feedback. Instead, the actual contact force is used to obtain a difference between the actual contact force of the ultrasound probe and the pressing force exerted on the handheld device, and the difference is displayed and prompted. This further emphasizes that the force feedback source in the present disclosure is the pressing force exerted on the handheld device by the physician while moving the handheld device on the working plane. This method of utilizing the reactive force of the pressing force for force feedback is timely and efficient, providing a direct haptic experience for the physician during ultrasound scanning.

The master computer 2 communicates with the data transceiver unit 8 through a 5G network or the like. The master computer 2 is configured to send the trajectory information and the pressing force to the data transceiver unit 8, and the data transceiver unit 8 is configured to send the trajectory information and pressing force to the slave scanning robot.

The slave ultrasound device is configured to perform an ultrasound scanning, collect an ultrasound image, and send the ultrasound image to the data transceiver unit 8, and the data transceiver unit 8 is configured to send the ultrasound image to the master computer 2.

The slave scanning robot includes a robotic arm 31 and a controller 32 configured to control a movement of the robotic arm 31. The slave ultrasound device includes an ultrasound probe 4 provided on an end of the robotic arm 31. The controller 32 is connected to the data transceiver unit 8 and receive the trajectory information of the handheld device 1 and the pressing force exerted on the handheld device 1.

The controller 32 is configured to control a movement of an end effector of the robotic arm 31 in a horizontal plane based on the velocity information of the handheld device 1 moving on the working plane such that a movement velocity of the ultrasound probe 4 at the end of the robotic arm 31 in the horizontal plane is the same as a movement velocity of the handheld device 1 on the working plane. That is, the controller 32 is configured to adjust the movement velocity of the ultrasound probe 4 at the end of the robotic arm 31 in the horizontal plane to follow the velocity of the handheld device 1 on the working plane based on a predetermined velocity mapping ratio coefficient. The controller 32 is further configured to control an orientation movement of the end effector of the robotic arm 31 in space based on the angular velocity information of the rotation of the handheld device 1 in space such that a rotational angular velocity of the ultrasound probe 4 at the end of the robotic arm 31 in space is the same as a rotational angular velocity of the handheld device 1 in space. That is, the controller 32 is configured to adjust the rotational angular velocity of the ultrasound probe 4 at the end of the robotic arm 31 in space to follow the rotational angular velocity of the handheld device 1 in space based on a predetermined angular velocity mapping ratio coefficient. The handheld device 1 is configured to obtain the pressing force exerted on the handheld device 1 through the pressure sensor, and the controller 32 is configured to control, based on the pressing force exerted on the handheld device 1, the end effector of the robotic arm 31 to move along a normal direction of a scanning surface such that a contact force between the ultrasound probe 4 at the end of the robotic arm 31 and a scanned region of a human body (i.e., an actual contact force of the ultrasound probe 4) is the same as the pressing force exerted on the handheld device 1.

The horizontal plane refers to a plane that is parallel to a plane on which the scanning robot is located, such as a plane parallel to a scanning bed. The scanning surface refers to a surface on which the ultrasound probe at the end of the slave scanning robot performs a scanning on a scanned region of the human body. The normal direction of the scanning surface refers to a direction perpendicular to the scanning surface.

Based on the velocity information of the handheld device moving on the working plane and the angular velocity information of the rotation of the handheld device in space, the handheld device of the present disclosure controls the movement of the end effector of the robotic arm in the horizontal plane and the orientation movement of the end effector of the robotic arm in space. That is, continuity of the entire movement process of the slave remote scanning robot is improved through a velocity mapping.

The controller 32 is configured to send the actual contact force of the ultrasound probe 4 to the data transceiver unit 8, and the data transceiver unit 8 is configured to send the actual contact force of the ultrasound probe 4 to the master computer 2.

The data transceiver unit 8 includes a robot data interface for data transmission with the slave scanning robot and an ultrasound data interface for data transmission with the slave ultrasound device.

In the present disclosure, the handheld device 1 is an imitation ultrasound probe with an integrated design and includes a housing and a velocity collection module, and an angular velocity collection module, a force collection module, a vibration module, a display, a data processing module, and a pressing module provided on the housing.

The velocity collection module adopts a velocity sensor, such as a photoelectric velocity sensor, and is provided inside the housing. The housing is provided with a velocity detection window, and a photoelectric detection end of the velocity collection module is aligned with the velocity detection window. Through the velocity detection window, photoelectric detection is performed to obtain the velocity information of the handheld device moving on the working plane.

The handheld device of the present disclosure may operate on any working surface, such as a desktop, a surface of a human skin model, a surface of the human body etc., without an auxiliary device such as a touchscreen. The velocity information of the handheld device moving on the working plane is directly obtained through the photoelectric velocity sensor inside the handheld device such that the control of the movement of the end effector of the robotic arm on the horizontal plane may be implemented based on the speed information.

The angular velocity collection module adopts an angular velocity sensor, such as an orientation angular velocity sensor, and is provided in the housing and configured to obtain the angular velocity information of the rotation of the handheld device 1 in space, i.e., to obtain angular velocity information of the handheld device rotating around an x axis, a y axis, and a z axis in space, wherein the x and y axes constitute the horizontal plane, the z axis is a vertical direction perpendicular to the horizontal plane, and the velocity information of the handheld device moving on the working plane includes velocity information along the x axis and velocity information along the y axis. The force collection module, i.e., the pressure sensor, is connected to the pressing module and configured to collect the pressing force exerted on an outer surface of the pressing module (i.e., a pressing surface of the handheld device) to obtain the pressing force exerted on the handheld device.

The velocity collection module, the angular velocity collection module, and the force collection module are all connected to the data processing module and respectively send the velocity information of the handheld device moving on the working plane, the angular velocity information of the rotation of the handheld device in space, and the pressing force exerted on the handheld device to the data processing module.

The data processing module is connected to the master computer 2 and sends the velocity information of the handheld device 1 moving on the working plane, the angular velocity information of the rotation of the handheld device 1 in space, and the pressing force exerted on the handheld device to 1 to the controller 32 of the slave scanning robot through the master computer 2 and the data transceiver unit 8.

The master computer 2 also sends the actual contact force data of the ultrasound probe 4 to the data processing module in real-time.

The data processing module is connected to the display and configured to send the pressing force exerted on the handheld device, the actual contact force of the ultrasound probe, and a difference between the actual contact force of the ultrasound probe and the pressing force exerted on the handheld device to the display in real-time for display. A real-time display of the pressing force exerted on the handheld device, the actual contact force of the ultrasound probe, and the difference between the actual contact force of the ultrasound probe and the pressing force exerted on the handheld device on the display provides the physician with clearer and more intuitive observation such that the physician obtains a tracking error between the actual contact force of the ultrasound probe and the pressing force exerted on the handheld device and receives a feedback of the force, which is convenient for the physician to adjust the pressing force exerted on the handheld device 1 in time.

The tracking error refers to a difference between the actual contact force of the ultrasound probe and a force that the user expects the ultrasound probe to exert on the scanned region of the human body. The feedback of the force refers to a correction value for the pressing force.

In some embodiments, the data processing module in the handheld device is further configured to, based on an ultrasound image obtained during a current ultrasound scan, obtain an expected recommended pressing force through a pressing force determination model and transmit the recommended pressing force to the physician. The ultrasound image refers to a visualized image captured by an ultrasound probe and processed by a Doppler ultrasound device. The pressing force determination model is a machine learning model that may be pre-stored in the data processing module.

In some embodiments, the pressing force determination model may be any one of a deep neural networks (DNN) model, a convolutional neural network (CNN) model, other custom model structures, or a combination thereof.

In some embodiments, an input of the pressing force determination model may include an ultrasound image during an ultrasound scanning process, and an output may be the recommended pressing force.

In some embodiments, the pressing force determination model may be obtained through training based on first training samples with a large count of first labels. The first training samples include ultrasound scan images, and the first labels include actual pressing forces applied during ultrasound probe scanning corresponding to the first training samples. The first labels may be obtained by collecting actual pressing forces applied by a professional ultrasound physician during a scan. For example, the actual pressing forces of the ultrasound probe may be obtained by sensor(s) on the slave scanning robot.

In some embodiments of the present disclosure, the data processing module is configured to obtain ultrasound image(s) of a current scanned region and provide the expected recommended pressing force for the current scanned region using the trained pressing force determination model. In some embodiments, the data processing module may display the determined expected recommended pressure in real-time to the physician on a screen, assisting the physician in adjusting the current scanning contact force according to the expected recommended pressure to obtain accurate ultrasound scan image(s) and improve the efficiency of ultrasound scanning.

The data processing module is connected to the vibration module and configured to send the difference between the actual contact force of the ultrasound probe and the pressing force exerted on the handheld device to the vibration module. The vibration module is configured to generate vibrations according to the difference between the actual contact force of the ultrasound probe and the pressing force exerted on the handheld device, wherein the vibration module generates the vibrations when the difference is greater than a threshold, and the greater the difference, the greater the intensity of the vibrations. In the present disclosure, the vibration module generates vibrations of varying intensity according to the difference between the actual contact force of the ultrasound probe and the pressing force exerted on the handheld device so as to provide the force feedback, which is convenient for the physician to adjust the pressing force exerted on the handheld device 1 in time.

The handheld device of the present disclosure adopts an integrated design such that the handheld device may operate on any working plane without an auxiliary device such as a touchscreen. The handheld device may be connected to a computer to form a device on the physician's end, i.e., the master device, with a simple structure, which is easy to carry and facilitates ultrasound scanning on the patient in a home environment.

In the present disclosure, a robotic arm mechanism 3 of the slave scanning robot includes the robotic arm 31, the controller 32 configured to control the movement of the robotic arm 31, a gripping mechanism 33 provided at an end of the robotic arm 31, a depth camera 34 provided at the end of the robotic arm 31, and a torque sensor 35 provided on the robotic arm 31.

The robotic arm 31 is a multi-joint compliance robotic arm.

The controller 32 is connected to the data transceiver unit 8 and configured to receive the trajectory information of the handheld device 1 and the pressing force exerted on the handheld device 1 sent by the master computer 2 through the data transceiver unit 8.

The controller 32 is configured to control the movement of the end effector of the robotic arm 31 in the horizontal plane, the orientation movement of the end effector of the robotic arm 31 in space, and a movement of the end effector of the robotic arm 31 along the normal direction of the scanning surface based on the trajectory information of the handheld device 1 and the pressing force exerted on the handheld device 1.

The torque sensor 35 is configured to obtain a joint torque of the robotic arm. The controller 32 is connected to the torque sensor 35 and configured to determine, based on the joint torque of the robotic arm 31 obtained by the torque sensor 35, the contact force between the ultrasound probe 4 at the end of the robotic arm 31 and the scanned region of the human body (i.e., the actual contact force of the ultrasound probe 4). The joint torque refers to a force that causes a joint of the robotic arm to rotate.

In the present disclosure, the joint torque is accurately obtained through the torque sensor 35 such that the contact force between the ultrasound probe at the end of the robotic arm and the scanned region of the human body is determined, which facilitates a precise control of the contact force between the ultrasound probe and the scanned region of the human body. In the present disclosure, a joint of the slave scanning robot is provided with the torque sensor, which facilitates joint force control and full-process compliance control, thereby ensuring patient safety.

The controller 32 is also connected to the gripping mechanism 33 and is configured to control a gripping action and a releasing action of the gripping mechanism 33. The controller 32 is provided with a control program for gripping and releasing the ultrasound probe 4. The controller 32 receives a gripping command or a releasing command from the master computer 2 through the data transceiver unit 8 and then controls the gripping action or the releasing action of the gripping mechanism 33 accordingly such that the physician remotely controls the gripping mechanism 33 to grip and replace the ultrasound probe 4, and to automatically apply a coupling agent to the ultrasound probe 4.

In some embodiments, the master computer may send an alert message to the physician based on a detection result obtained through a coupling agent detection technique. For example, the alert message may include information indicating insufficient coupling agent at one or more scanning locations. Exemplary coupling agent detection techniques may include a confidence detection based on ultrasound image(s).

In some embodiments, real-time confidence detection based on ultrasound image(s) of the coupling agent application may be performed during a scanning process. And whether to perform a normal scan or additional coupling agent is needed may be determined based on a detection result. Specifically, the confidence detection may include the following operations:

Operation 1: An ultrasound image may be obtained in real time, the ultrasound image may be divided vertically into a left region and a right region from a center, and image confidences for the left and right regions may be determined.

Operation 2:

Operation 2.1: When the image confidences in the left and right regions are both less than a set threshold, it may indicate a presence of a dark region on both the left and right regions of the ultrasound image and poor image quality. A friction force magnitude and a scanning force magnitude in a scanning tangent direction are obtained through a force sensor.

Operation 2.1.1: If the friction force in the scanning tangent direction is less than a threshold and the scanning force is less than a maximum safe scanning force, the scanning force may be increased and Operation 1 may be executed again.

Operation 2.1.2: If the friction force in the scanning tangent direction is larger than a threshold or the scanning force is larger than the maximum safe scanning force, it may indicate that the coupling agent is insufficient and reapplication may be needed, and Operation 1 may be executed again.

Operation 2.2: When the image confidence in only one of the left and right regions is less than the threshold, which indicates the presence of a dark region on the region of the ultrasound image where the image confidence is less than the threshold and poor skin contact between the ultrasound probe and the skin, the robotic arm may be controlled to adjust the posture of the ultrasound probe such that the ultrasound probe may be rotated a certain angle towards the region where the image confidence is less than the threshold and Operation 1 may be executed again.

Operation 2.3: When the image confidences in both the left and right regions are larger than the threshold, the scan is performed normally.

The end of the robotic arm 31 is provided with the depth camera 34 configured to capture a depth image. The depth camera 34 is connected to the controller 32 and configured to send the depth image to the controller 32, and the controller 32 is configured to send the depth image to the master computer 2 through the data transceiver unit 8.

In the present disclosure, the master computer 2 is configured to perform a three-dimensional reconstruction based on the depth image to obtain a three-dimensional model. The master computer 2 displays the three-dimensional model for the convenience of the physician's observation. The master computer 2 may set a movement trajectory based on the three-dimensional model and send the movement trajectory to the controller 32 through the data transceiver unit 8. The controller 32 controls the end effector of the robotic arm 32 to move along the movement trajectory such that the ultrasound probe at the end of the robotic arm reaches a designated position without collision, for example, reaches a position above the surface of the human body for the convenience of the physician's further observation and operation. An initial position of the robotic arm 31 is above, but at a considerable distance from the surface of the human body, or at a side of the surface of the human body. In such cases, based on the depth image, the end of the robotic arm 31 is moved from the initial position to the designated position above the surface of the human body, which facilitates the physician's further observation and operation. The designated position may be preset based on needs.

The depth camera 34 is further configured to capture a depth image of the surface of the human body and send the depth image of the surface of the human body to the master computer 2 through the data transceiver unit 8.

The master computer 2 performs a three-dimensional reconstruction of the human body based on the depth image of surface of the human body, and obtains a three-dimensional model of the human body. The three-dimensional model of the human body may include a model of the scanned region and other parts of the body outside the scanned region. The master computer 2 displays the three-dimensional model of the human body, which facilitates the physician's observation of undulations of the surface of the human body. The master computer 2 is configured to, based on the three-dimensional model of the human body, set an initial position for ultrasound scanning of the scanned region of the human body, generate a collision-free path for the robotic arm from a current position to the initial scanning position based on the three-dimensional model and a path planning algorithm, and send the collision-free path to the controller 32 through the data transceiver unit 8. The collision-free path refers to a movement path of the robotic arm that avoids collisions with the human body or other obstacles. For example, a movement path of the robotic arm 31 ensuring that the robotic arm 31 does not collide with the torso, head, or other parts before reaching a neck scanning region. The controller 32 is configured to control the end effector of the robotic arm 31 to move along the collision-free path such that the ultrasound probe 4 at the end of the robotic arm 31 automatically reaches the initial position for ultrasound scanning. For example, during a non-scanning process, regions such as the stomach and the chest are identified automatically. By setting the initial position for ultrasound scanning of the scanned region of the human body and generating the collision-free path for the robotic arm from the current position to the initial scanning position based on the three-dimensional model and the path planning algorithm, when the physician chooses to set the end of the robotic arm to reach a position above a designated region, i.e., the initial position for ultrasound scanning, the controller 32 controls the robotic arm 31 to move along the collision-free path such that the ultrasound probe 4 at the end of the robotic arm 31 automatically reaches the designated region specified by the physician, which facilitates the scanning operation. In some embodiments, the collision-free path may also be applied after the ultrasound scanning. The controller 32 may control the end effector of the robotic arm 31 to move along the collision-free path, allowing the ultrasound probe 4 at the end of the robotic arm 31 to automatically return to the initial position of the ultrasound scanning, which facilitates the remote ultrasound scanning operation of the physician.

After the robotic arm 31 of the slave scanning robot is powered on, an entire movement process includes a non-ultrasound scanning process and an ultrasound scanning process. The non-ultrasound scanning process refers to a process where the controller 32 controls the movement of the robotic arm 31 such that the ultrasound probe 4 reaches the scanned region of the human body, and during the non-ultrasound scanning process, the ultrasound probe 4 does not contact the scanned region of the human body, and the actual contact force of the ultrasound probe 4 is zero. The ultrasound scanning process refers to a process where the controller 32 controls the movement of the robotic arm 31 such that the ultrasound probe 4 performs the ultrasound scanning on the scanned region of the human body, and during the ultrasound scanning process, the ultrasound probe 4 contacts the scanned region of the human body, and the actual contact force of the ultrasound probe 4 is greater than zero.

In the portable remote ultrasound scanning system of the present disclosure, an entire movement process of the robotic arm 31 is performed through a compliance control. The compliance control refers to actively controlling the robotic arm 31 using a certain control strategy such that the robotic arm 31 is compliant to an external force when contacting an external environment. A compliance control method for safe ultrasound scanning is as follows:

In some embodiments, the compliant control includes at least two aspects: (1) controlling the contact force between the ultrasound probe and a scanning plane in a normal direction of the scanning plane. A magnitude of the contact force is equal to the pressing force applied by the physician on the working plane of the handheld device. When the reactive force at contact is greater than the contact force applied by the compliant control of the robotic arm, the end of the robotic arm moves in the opposite direction of the contact force until the contact force and the reactive force are balanced. When the reactive force at contact is less than the contact force applied by the compliant control of the robotic arm, the end of the robotic arm moves in the direction of the contact force until the contact force and the reactive force are balanced. (2) In any tangent direction of the scanning plane, the movement of the robotic arm adopts an impedance control. When an external force greater than a predetermined threshold acts on the robotic arm in any tangent direction, the end of the robotic arm generates an elastic displacement in the tangent direction and a reactive force in an opposite direction of the applied force. The reactive force balances with the external force, and a magnitude of the reactive force is proportional to the elastic displacement. When the reactive force disappears, the robotic arm returns to its original state.

During the non-ultrasound scanning process, the movement of the robotic arm 31 adopts an impedance control, i.e., the movement of the end effector of the robotic arm 31 in the horizontal plane and the movement of the end effector of the robotic arm 31 along the normal direction of the scanning surface are performed through the impedance control, with different impedance in the horizontal plane and along the normal direction of the scanning surface. During the ultrasound scanning process, the movement of the robotic arm 31 adopts a hybrid control of the impedance control and a constant force control, i.e., the movement of the end effector of the robotic arm 31 in the horizontal plane is performed through the impedance control, and the movement of the end effector of the robotic arm 31 along the normal direction of the scanning surface is performed through the constant force control.

During the ultrasound scanning process, a desired force value for the constant force control of the end effector of the robotic arm 31 in the normal direction of the scanning surface is obtained by mapping the pressing force exerted on the handheld device 1. The mapping of the desired force value for the constant force control may be obtained in two mapping manners: a variable force segmental mapping and a variable force continuous mapping, and the two mapping manners may be switched in an actual operation process.

The variable force segmental mapping refers to a process where the pressing force exerted on the handheld device 1 is divided into different segments and each segment is mapped to the controller 32, and the controller 32 controls the movement of the robotic arm 31 to drive the ultrasound probe 4 to perform the ultrasound scanning on the scanned region of the human body, wherein when the pressing force exerted on the handheld device 1 falls within a certain segment, the desired force value for the constant force control remains unchanged and the desired force value is a certain value within the segment; and when the pressing force exerted on the handheld device 1 switches to a different segment, the desired force value for the constant force control changes accordingly to a certain value within the different segment. The variable force continuous mapping refers to a process where the pressing force exerted on the handheld device 1 is mapped to the controller 32 directly, and the controller 32 controls the movement of the robotic arm 31 to drive the ultrasound probe 4 to perform the ultrasound scanning on the scanned region of the human body, wherein the desired force value for the constant force control changes continuously according to the pressing force exerted on the handheld device 1. The desired force value is an expected value of the actual contact force when the pressing force is applied.

The entire movement process of the robotic arm of the present disclosure is performed through the compliance control, which may ensure patient safety. The handheld device of the present disclosure utilizes the pressing force to control the movement of the end effector of the robotic arm along the normal direction of the scanning surface. The variable force continuous mapping is used to ensure the continuity of the contact force between the ultrasound probe and the human body.

In the present disclosure, a slave ultrasound device includes the ultrasound probe 4 and an ultrasound scanning host 5. The ultrasound probe 4 is connected to the ultrasound scanning host 5, and the ultrasound scanning host 5 is connected to the data transceiver unit 8.

The ultrasound probe 4 is configured to perform an ultrasound scanning, collect an ultrasound image, and send the ultrasound image to the ultrasound scanning host 5. The ultrasound scanning host 5 is configured to send the ultrasound image to the master computer 2 through the data transceiver unit 8, and the master computer 2 is configured to display the ultrasound image collected by the ultrasound probe 4 in real-time.

The master computer 2 is also configured to set a scanning parameter(s) of the ultrasound scanning host 5 and send the scanning parameter to the ultrasound scanning host 5 through the data transceiver unit 8. The scanning parameter refers to a relevant control parameter of the ultrasound scanning host 5 in the ultrasound scanning. The ultrasound scanning host 5 controls the ultrasound scanning of the ultrasound probe 4 based on the scanning parameter sent by the master computer 2.

The slave environment sensing unit includes a global camera 7 and a communication device 6.

The global camera 7 is configured to obtain a live video of a slave end, i.e., the patient's end of the ultrasound scanning, including an overall video of the slave scanning robot and a position and orientation video of the robotic arm 31. The global camera 7 is connected to the data transceiver unit 8 and configured to send the overall video of the slave scanning robot and the position and orientation video of the robotic arm 31 to the data transceiver unit 8. The data transceiver unit 8 is configured to send the overall video of the slave scanning robot and the position and orientation video of the robotic arm 31 to the master computer 2 through the 5G network, and the master computer 2 is configured to display the overall video of the slave scanning robot and the position and orientation video of the robotic arm 31 in real-time.

The communication device 6 is connected to the master computer 2 for real-time communication between the physician and the patient. The communication device 6 includes a microphone and a speaker.

In the present disclosure, by displaying the depth image of the surface of the human body, the three-dimensional model of the human body, the overall video of the slave scanning robot and the position and orientation video of the robotic arm, it is convenient for the physician to observe an overall situation of the slave scanning robot, the position and orientation of the robotic arm, the undulations of the surface of the human body, and a specific situation of the scanned region of the human body, thereby creating a visual presence sense when the physician performs the remote ultrasound scanning.

In the present disclosure, a sense of auditory and forceful presence is created through the communication device, the torque sensor, the display, and the vibration module when the physician remotely controls the slave scanning robot to perform the ultrasound scanning.

The slave scanning robot and the slave ultrasound device of the present disclosure are two independent devices. Data of the two devices is merged through the data transceiver unit and transmitted to the master computer. The slave scanning robot may be applied to various types of ultrasound devices and may be combined with different ultrasound scanning devices in different hospitals for ultrasound scanning. Additionally, the slave scanning robot may also be adapted to a portable ultrasound scanning device.

In the present disclosure, communication between the master device and the slave device is performed through a network (e.g., the 5G network). Both the master device and the slave device send data to be transmitted to a corresponding base station through a communication device (e.g., a 5G communication device). The base station then uploads the data to be transmitted to a cloud server. Both the master device and the slave device obtain data to be received from the cloud server through the communication device and the corresponding base station.

The above is merely a preferred embodiment of the present disclosure and should not be construed as limiting the scope of the present disclosure. Any modifications, equivalent substitutions, improvements, etc., made within the spirit and principles of the present disclosure should be included within the scope of protection of the present disclosure.

What is claimed is:

1. A portable remote ultrasound scanning system, comprising a master device and a slave device, wherein
the master device includes a handheld device (1) and a master computer (2) connected to the handheld device (1), wherein the handheld device (1) is a mimetic ultrasound probe;
the slave device includes a slave scanning robot, a slave ultrasound device, and a data transceiver unit (8) connected to the slave scanning robot and the slave ultrasound device respectively, wherein the data transceiver unit (8) includes a robot data interface for data transmission with the slave scanning robot and an ultrasound data interface for data transmission with the slave ultrasound device;
when a physician holds the handheld device (1) to move on a working plane which refers to a surface of an object with which the handheld device contacts, the handheld device (1) is configured to send trajectory information of the handheld device (1) to the master computer (2), the handheld device (1) is configured further to send a pressing force, which refers to a force between the handheld device and the working plane, exerted on the handheld device (1) to the master computer (2), the trajectory information of the handheld device (1) including velocity information of the handheld device (1) moving on the working plane and angular velocity information of a rotation of the handheld device in space, the velocity information of the handheld device (1) moving on the working plane being obtained through a photoelectric velocity sensor, and the angular velocity information of the rotation of the handheld device in space being obtained through an orientation and angular velocity sensor;
the master computer (2) communicates with the data transceiver unit (8), and the master computer (2) is configured to send the trajectory information of the handheld device (1) and the pressing force exerted on the handheld device (1) to the data transceiver unit (8);

the slave ultrasound device is configured to perform an ultrasound scanning, collect an ultrasound image, and send the ultrasound image to the data transceiver unit (8), and the data transceiver unit (8) is configured to send the ultrasound image to the master computer (2);

the slave ultrasound device includes an ultrasound probe (4);

the slave scanning robot includes a robotic arm (31) and a controller (32) configured to control a movement of the robotic arm (31);

the ultrasound probe (4) is provided at an end of the robotic arm (31);

the data transceiver unit (8) is configured to send the trajectory information of the handheld device (1) and the pressing force exerted on the handheld device (1) to the controller (32);

the controller (32) is configured to control a movement of an end effector of the robotic arm (31) in a horizontal plane based on the velocity information of the handheld device (1) moving on the working plane such that a movement velocity of the ultrasound probe (4) at the end of the robotic arm (31) in the horizontal plane is the same as a movement velocity of the handheld device (1) on the working plane;

the controller (32) is configured to control an orientation movement of the end effector of the robotic arm (31) in space based on the angular velocity information of the rotation of the handheld device (1) in space such that a rotational angular velocity of the ultrasound probe (4) at the end of the robotic arm (31) in space is the same as a rotational angular velocity of the handheld device (1) in space;

the controller (32) is configured to control, based on the pressing force exerted on the handheld device (1), the end effector of the robotic arm (31) to move along a normal direction of a scanning surface such that a contact force between the ultrasound probe (4) at the end of the robotic arm (31) and a scanned region of a human body is the same as the pressing force exerted on the handheld device (1), wherein the contact force refers to an actual contact force of the ultrasound probe (4);

an entire movement process of the robotic arm (31) is performed through a compliance control, wherein the compliance control refers to actively controlling the robotic arm (31) using a control strategy such that the robotic arm (31) is compliant to an external force when contacting an external environment;

during a non-ultrasound scanning process, the movement of the robotic arm (31) adopts an impedance control, wherein the movement of the end effector of the robotic arm (31) in the horizontal plane and a movement of the end effector of the robotic arm (31) along the normal direction of the scanning surface are performed through the impedance control;

during an ultrasound scanning process, the movement of the robotic arm (31) adopts a hybrid control of the impedance control and a constant force control, wherein the movement of the end effector of the robotic arm (31) in the horizontal plane is performed through the impedance control, and the movement of the end effector of the robotic arm (31) along the normal direction of the scanning surface is performed through the constant force control;

during the ultrasound scanning process, the pressing force exerted on the handheld device (1) is converted to a desired force value for the constant force control through a variable force segmental mapping or variable force continuous mapping, and the contact force between the ultrasound probe (4) and the scanned region of the human body follows the desired force value, the desired force value is an expected value of actual contact force when pressing force is applied; wherein the variable force segmental mapping refers to a process where the pressing force exerted on the handheld device (1) is divided into different segments and each segment is mapped to the controller (32), and the controller (32) controls the movement of the robotic arm (31) to drive the ultrasound probe (4) to perform the ultrasound scanning on the scanned region of the human body, wherein when the pressing force exerted on the handheld device (1) falls within a certain segment, the desired force value for the constant force control remains unchanged and the desired force value is a certain value within the segment; and when the pressing force exerted on the handheld device (1) switches to a different segment, the desired force value for the constant force control changes accordingly to a certain value within the different segment; and the variable force continuous mapping refers to a process where the pressing force exerted on the handheld device (1) is continuously mapped to the controller (32) in proportion, and the controller (32) controls the movement of the robotic arm (31) to drive the ultrasound probe (4) to perform the ultrasound scanning on the scanned region of the human body, wherein the desired force value for the constant force control changes continuously following continuous changes of the pressing force exerted on the handheld device (1);

the end of the robotic arm (31) is provided with a depth camera (34) configured to capture a depth image; and the depth camera (34) is connected to the controller (32) and configured to send the depth image to the controller (32), and the controller (32) is configured to send the depth image to the master computer (2) through the data transceiver unit (8);

the depth camera (34) is configured to capture the depth image of a surface of the human body; the master computer (2) is configured to perform a three-dimensional modeling of the human body based on the depth image of the surface of the human body to obtain a three-dimensional model of the human body; the master computer (2) is configured to identify the scanned region of the human body based on the three-dimensional model of the human body, set an initial position for ultrasound scanning of the scanned region of the human body, generate a collision-free path for the robotic arm from a current position to the initial scanning position based on the three-dimensional model and a path planning algorithm, wherein the collision-free path refers to a movement path of the robotic arm that avoids collisions with human body or other obstacles, and send the collision-free path to the controller (32) through the data transceiver unit (8); and the controller (32) is configured to control the end effector of the robotic arm (31) to move along the collision-free path such that the ultrasound probe (4) at the end of the robotic arm (31) automatically reaches the initial position for ultrasound scanning.

2. The portable remote ultrasound scanning system of claim 1, wherein
the movement velocity of the end effector of the robotic arm (31) in the horizontal plane is controlled to follow the movement velocity of the handheld device (1) on the working plane based on a predetermined velocity mapping ratio coefficient.

3. The portable remote ultrasound scanning system of claim 1, wherein
the controller (32) is configured to send the actual contact force of the ultrasound probe (4) to the data transceiver unit (8), the data transceiver unit (8) is configured to send the actual contact force of the ultrasound probe (4) to the master computer (2), and the master computer (2) is configured to send the actual contact force of the ultrasound probe (4) to the handheld device (1);
the handheld device (1) is provided with a display configured to display the actual contact force of the ultrasound probe (4), the pressing force exerted on the handheld device (1), and a difference between the actual contact force of the ultrasound probe (4) and the pressing force exerted on the handheld device (1) in real-time; and
the handheld device (1) is further provided with a vibration processor, the vibration processor being configured to generate vibrations according to the difference between the actual contact force of the ultrasound probe (4) and the pressing force exerted on the handheld device (1), wherein the vibration processor generates the vibrations when the difference is greater than a threshold, and the greater the difference, the greater the intensity of the vibrations.

4. The portable remote ultrasound scanning system of claim 1, wherein
the slave device further includes a slave environment sensing unit;
the slave environment sensing unit includes a global camera (7) and a communication device (6);
the global camera (7) is configured to obtain an overall video of the slave scanning robot and a position and orientation video of the robotic arm (31); the global camera (7) is connected to the data transceiver unit (8) and configured to send the overall video of the slave scanning robot and the position and orientation video of the robotic arm (31) to the master computer (2) through the data transceiver unit (8) such that the overall video of the slave scanning robot and the position and orientation video of the robotic arm (31) are displayed on the master computer (2) in real-time; and
the communication device (6) is configured to realize real-time communication between the physician and a patient, wherein the communication device (6) includes a microphone and a speaker.

5. The portable remote ultrasound scanning system of claim 3, wherein
the robotic arm (31) is provided with a torque sensor (35) configured to obtain a joint torque of the robotic arm (31),
the controller (32) is connected to the torque sensor (35) and configured to determine, based on the joint torque of the robotic arm (31) obtained by the torque sensor (35), the contact force between the ultrasound probe (4) at the end of the robotic arm (31) and the scanned region of the human body.

6. A compliance control method for safe ultrasound scanning applied in the portable remote ultrasound scanning system of claim 1, wherein
the non-ultrasound scanning process refers to a process where the controller (32) controls the movement of the robotic arm (31) such that the ultrasound probe (4) reaches the scanned region of the human body, and during the non-ultrasound scanning process, the contact force between the ultrasound probe (4) and the scanned region of the human body is zero; and
the ultrasound scanning process refers to a process where the controller (32) controls the movement of the robotic arm (31) such that the ultrasound probe (4) performs the ultrasound scanning on the scanned region of the human body, and during the ultrasound scanning process, the actual contact force between the ultrasound probe (4) and the scanned region of the human body is greater than zero.

7. The portable remote ultrasound scanning system of claim 1, wherein
the handheld device (1) is further configured to, based on an ultrasound image obtained during a current ultrasound scan, obtain an expected recommended pressing force through a pressing force determination model and transmit the recommended pressing force to the physician, and the pressing force determination model is a machine learning model.

8. The portable remote ultrasound scanning system of claim 1, wherein
the slave device has a coupling agent detection function which refers to real-time confidence detection based on ultrasound images of coupling agent application performed during a scanning process and determines whether to perform a normal scan or additional coupling agent is needed based on a detection result.

* * * * *